(12) United States Patent
Manison

(10) Patent No.: US 6,924,434 B2
(45) Date of Patent: Aug. 2, 2005

(54) PHYSIOLOGICAL EFFECT DEVICE

(76) Inventor: Philip John Manison, 97 Dunvant Road, Killay, Swansea (GB), SA2 7NN ( * ) Notice: Subject to any disclaimer, the term of this patent is extended or adjusted under 35 U.S.C. 154(b) by 0 days.

(21) Appl. No.: 10/399,937
(22) PCT Filed: Oct. 24, 2001
(86) PCT No.: PCT/GB01/04711
§ 371 (c)(1),
(2), (4) Date: Oct. 10, 2003
(87) PCT Pub. No.: WO02/34334
PCT Pub. Date: May 2, 2002

(65) Prior Publication Data
US 2004/0050577 A1 Mar. 18, 2004

(30) Foreign Application Priority Data
Oct. 24, 2000 (GB) .................................. 0025992
Nov. 15, 2000 (GB) .................................. 0027878
Mar. 14, 2001 (GB) .................................. 0106405

(51) Int. Cl.$^7$ ............................................... H01B 7/18
(52) U.S. Cl. ................................................... 174/108
(58) Field of Search ........................... 174/108, 128.1; 336/174; 600/10, 13, 14, 15

(56) References Cited

U.S. PATENT DOCUMENTS

| | | | |
|---|---|---|---|
| 3,489,974 A | * 1/1970 | Montross | 336/174 |
| 4,757,804 A | 7/1988 | Griffith et al. | 128/1.5 |
| 4,850,340 A | 7/1989 | Onishi | 128/24.1 |
| 5,085,626 A | * 2/1992 | Frey | 600/13 |
| 5,269,747 A | 12/1993 | Erickson et al. | 600/14 |
| 5,344,384 A | 9/1994 | Ostrow et al. | 600/13 |
| 5,518,495 A | 5/1996 | Kolt | 600/13 |
| 5,642,739 A | 7/1997 | Fareed | 128/881 |
| 5,997,464 A | * 12/1999 | Blackwell | 600/13 |
| 6,024,691 A | 2/2000 | Tepper et al. | 600/13 |
| 2002/0050906 A1 | * 5/2002 | Fedeli et al. | 336/174 |

FOREIGN PATENT DOCUMENTS

DE   35 12 729 A1 * 10/1986

OTHER PUBLICATIONS

European Patent Application Publication No. 0 271 423 Publ. Jun. 15, 1988 to Isidro Bocanegra Marquina.
UK Patent Application No. GB 2 087 709 Publ. Jun. 3, 1992 to Proyectos Magneticos, S.A. (Promag), inventor Leonardo Leprevost.
German Patent No. DE 3834849 Publ. Apr. 19, 1990 to Heinz Ridder (applicant), Gerhard Kaschik (inventor).
German Patent No. DE 3205048 Publ. Aug. 25, 1983 to Werner Kraus (applicant), Werner Kraus (inventor).
German Patent DE 19747608 Publ. Jan. 7, 1999 to Marco Schmidt (applicant).

* cited by examiner

Primary Examiner—Chau N. Nguyen
(74) Attorney, Agent, or Firm—Waddey & Patterson, P.C.; Emily A. Shouse

(57) ABSTRACT

A physiological effect device comprising an elongate flexible member, band or strip having a magnetically inductive core around which is coiled at least one insulated electrically conductive wire. The conductive wire can act as a solenoid and utilize the small electrical pulses normally sent around or through a subject (such as an animal) wearing the device and thereby induce a (therapeutic) magnetic field in the core. The device may provide a useful induced magnetic field for physiological effects even when at rest and/or may absorb electrical pulses (such as those associated with pain in an animal). The device may further be arranged to absorb or screen radiation (such as microwaves or the like).

7 Claims, 2 Drawing Sheets

PHYSIOLOGICAL EFFECT DEVICE

FIELD OF THE INVENTION

This invention relates to a physiological effect device, and in particular to such a device for use in treatment, alleviation or prophylaxis of ailments such as rheumatic pains, arthritis, neuralgia, lumbago and the like, in animals (including humans) or for influencing plant growth or the like (hereinafter, collectively "the subject").

BACKGROUND OF THE INVENTION

It is well known to provide a therapeutic wrist band of copper or brass which has a gap in it so that as the user's arm moves through the earth's magnetic field during the normal course of the user's daily activities, a very small voltage is set up in the wrist band, which is thought to alleviate discomfort caused by ailments such as rheumatism, arthritis etc.

However, conventional therapeutic wrist bands do not work when the user's arm is stationary, for example, when resting.

EP-A-0271423 and GB-A-2087709 both describe therapeutic wrist bands comprising an open elliptical or circular shaped band having permanent magnets of opposite polarities secured at each end. A magnetic flux is set up across the gap in the band between the two permanent magnets, which magnetic flux is considered to have therapeutic properties.

SUMMARY OF THE INVENTION

I have now devised an improved physiological effect device which comprises an elongate flexible member, band or strip which is comprised of a magnetically inductive core around which is coiled at least one insulated electrically conductive wire.

The conductive wire can act as a solenoid and utilise the small electrical pulses normally sent around or through a subject and thereby induce a (therapeutic) magnetic field in the core. The device may provide a useful induced magnetic field for physiological effects even when at rest and/or may absorb electrical pulses (such as those associated with pain in an animal). The device may further be arranged to absorb or screen radiation (such as microwaves or the like).

Known devices which provide a physiological effect are typically connected to a suitable power source to provide electromagnetic field therapy. The device of the present invention is capable of providing a therapeutic and/or physiological effect as described above without needing to be connected to a power source, making the device of the present invention cheap to make, easy to use and ecologically friendly compared to known devices.

The core is preferably of mild steel, electrical steel or iron (although inductive nickel or the like may be used in some circumstances), and is preferably in the form of a flexible member arranged to be wrapped around a portion of a subject, for example a human user's wrist or the like.

The device according to the invention may be incorporated into an item of clothing, such as a belt, or items of jewellery such as a watch strap, bracelet etc., when it is intended for human use.

Alternatively, the device may be arranged to be attached to a non-human animal (as described above), or to a plant (such as a tree) or the like.

The device may be incorporated into a band of material which can be fastened around, for example, a human's wrist or the joint or limb of a non-human animal, typically by a burr fastener such as velcro (TM).

Also in accordance with the present invention, there is provided a method of manufacturing a physiological effect device comprising the steps of coiling a length of electrically conductive wire around a central, magnetically inductive core. A series of such devices may be manufactured in the form of long lengths which are then cut to convenient lengths for use. In this embodiment, plastic end caps may be crimped or glued on to the cut ends of the core and the wire, so as to isolate the cut ends from one another. Means for securing said core around or against a portion of the subject may also be provided.

Exemplary embodiments of the invention will now be described with reference to the accompanying drawings, in which:

The elongate member, band or strip may be in the form of a flexible cable or wire, or alternatively, may be in the form of a mesh or grid created by weaving the elongate member band or strip into a mat-like structure.

The core is preferably provided with insulating end caps, so as to prevent inadvertent contact (and short-circuiting) between the ends of the core.

The insulated electrically conductive wire coiled around the core is preferably copper or aluminium wire, having an insulating sheath to isolate the wire from the core, and to insulate adjacent coils from one another. Alternatively fine titanium wire having an insulating sheath may be used to produce a thinner device. The coiled wire preferably extends along the length of the core, two or more such coils may be used if wished.

In some embodiments, a portable power supply, such as an electrical battery, may be provided to enable an electrical potential to supplement the induced field in the core. In such an embodiment, switching means is preferably provided so as to permit the core to be energised by the power supply when wished.

When the device of the present invention is intended as a therapeutic device for use with humans, it can be worn on the user's wrist, ankle, waist, neck, shoulders, or in any other convenient position to access the main location of the ailment to be treated then for use on a non-human animal, it may be worn around a joint, limb or the like.

DESCRIPTION OF THE PREFERRED EMBODIMENTS

Figure 1:
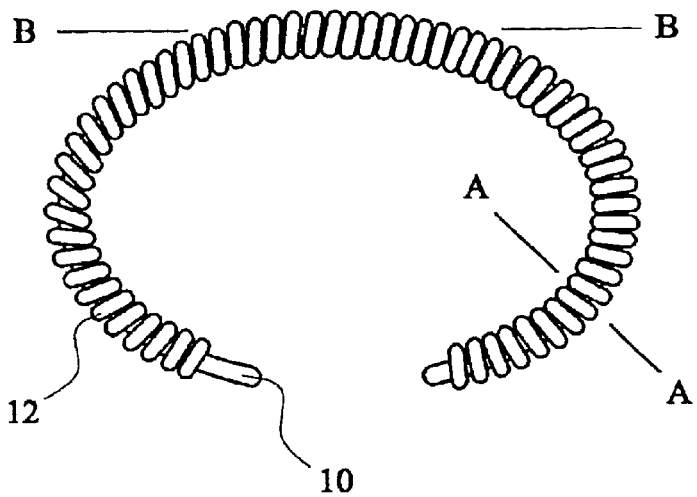
FIG. 1 is a plan view of a physiological effect device according to a first exemplary embodiment of the invention.
Figures 2, 3:
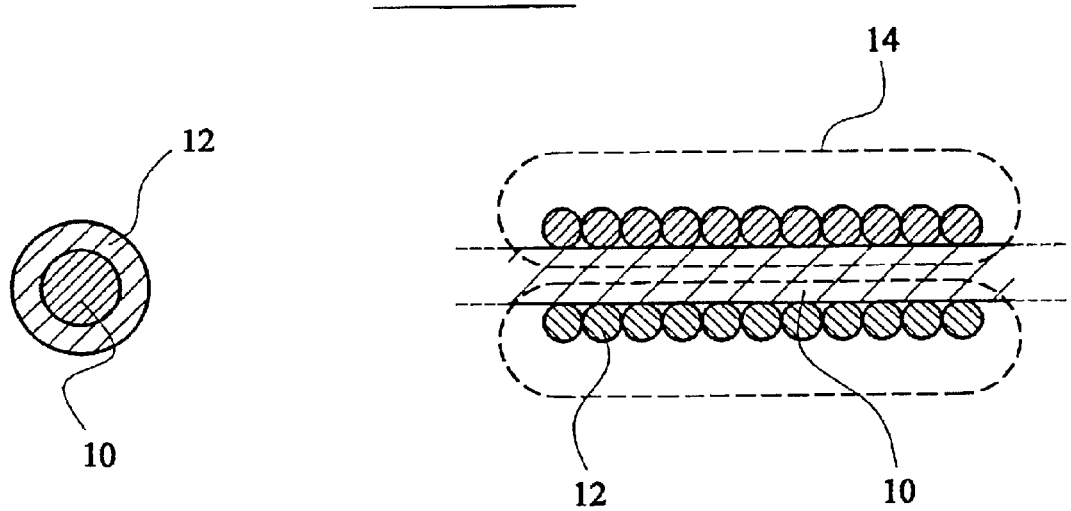
FIG. 2 is a cross-sectional view through line A—A of the device of FIG. 1.
FIG. 3 is a partial cross-sectional view through line B—B of the device of FIG. 1.

Referring to FIGS. 1 and 2 of the drawings, a physiological effect device according to a first exemplary embodiment of the invention comprises a core 10 of magnetically inductive material, such as mild steel, electrical steel or iron around which is wound (in the form of a coil) wire 12 of electrically conductive material, such as copper, aluminium or titanium. The conductive wire 12 is provided with an insulating sheath. The core 10 is bent into an open, substantially elliptical shape as illustrated in FIG. 1.

Referring to FIG. 3 of the drawings, when the device of FIG. 1 is worn on, for example, a human user's wrist, the device is believed to utilise electrical pulses sent by the brain to other parts of the user's body. The conductive wire coil 12 can act as a solenoid and sets up a magnetic flux 14 in the core 10, which magnetic flux is believed to have therapeutic properties.

Figure 4:
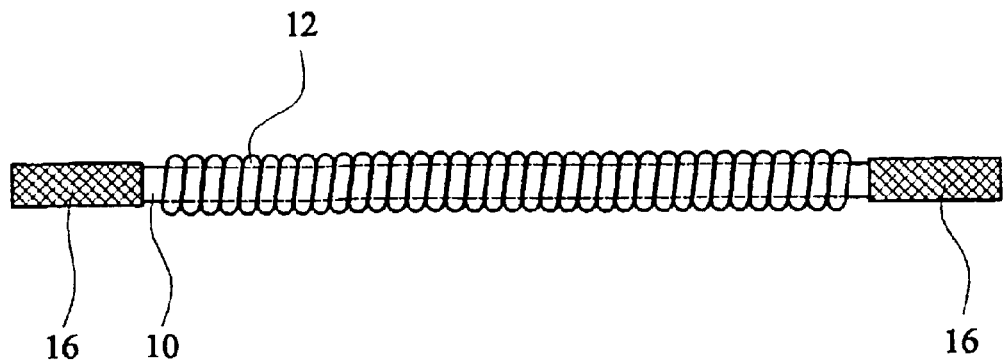
FIG. 4 is a plan view of a physiological effect device according to a second exemplary embodiment of the invention.

Referring to FIG. 4 of the drawings, the device of the present invention may be provided as a core 10 of magnetically conductive material, around which is wound a coil of an insulated, electrically conductive wire 12. The ends of the core 10 are provided with insulating end caps 16 to prevent contact between the ends of the core 10. The device may be held in place on a wrist, ankle etc. as required by the shape retaining characteristics of the metal constituting the core 10.

Figure 5:
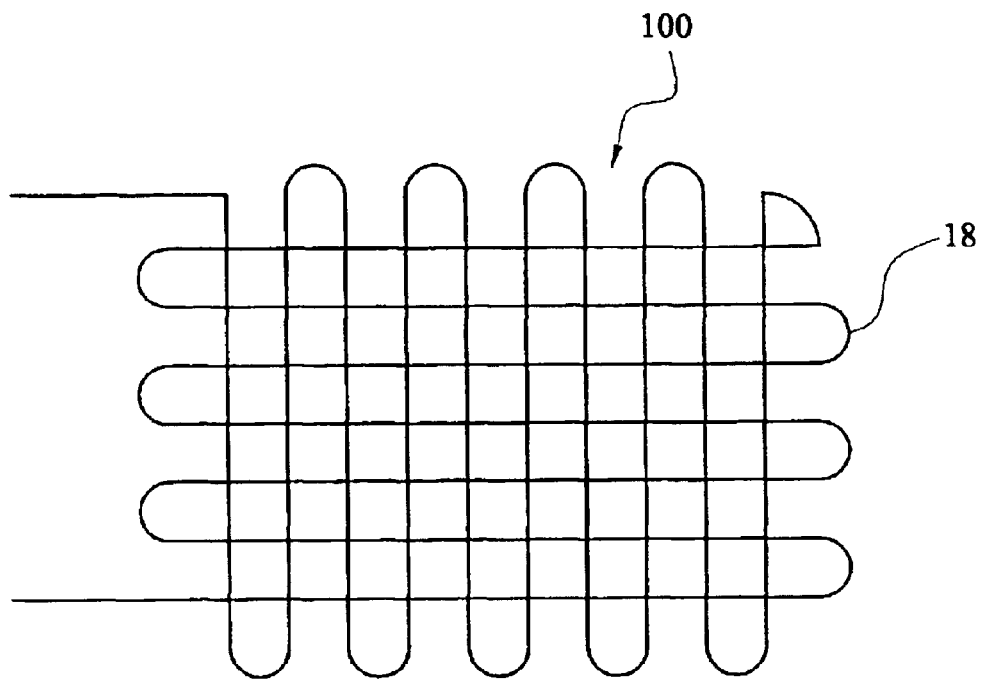
FIG. 5 is a schematic plan view of a first alternative core structure.
Figure 6:
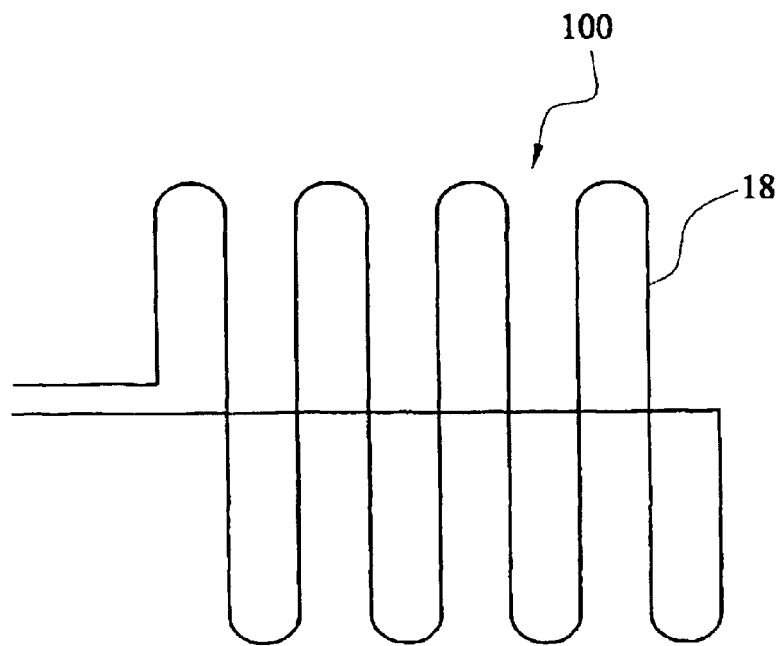
FIG. 6 is a schematic plan view of a second alternative core structure.

Referring to FIGS. 5 and 6 of the drawings, a band suitable for placing around a portion of a subject may be configured in the following manner. A core about which an electrically conductive wire is coiled, as described above, may be configured in the form of a mesh or a grid 100. The mesh or grid 100 is constructed by weaving said core/coiled wires into a mat-like structure (as illustrated by way of example in FIGS. 5 and 6). Preferably said mat-like structure is combined with a fabric or carrier material, so as to create a band which may be a affixed around a portion of a subject.

Incorporation of the core/coiled wire structure of the present invention with a fabric or carrier material is a preferred means of utilising the device of the present invention because it may result in a device that is simple and easy to use, visually attractive to the wearer (when that wearer is sentient), and robust.

It will be appreciated that the ends of the band 10 should not be allowed to come into electrical contact with each other for the device to be effective. Similarly the coiled conductive wire should not come into electrical contact with the core, and adjacent turns of the coiled wire should not come into electrical contact with one another.

What is claimed is:

1. A physiological effect device to be used in therapy of a wearer of the said device comprising an elongate flexible member, band or strip to be positioned around a portion of the body of the wearer said flexible member, band or strip having a magnetically inductive core around which is coiled at least one insulated electrically conductive wire, wherein said core has insulating end caps such that said core can be energised by electrical impulses picked up from the body of the wearer without short circuiting between the ends of the core and without the need for a power supply to be connected to the device to energise the core.

2. A device according to claim 1, in which the core is of mild steel, electrical steel or iron.

3. A device according to claim 1, in which the elongate flexible member, band or strip is in the form of a flexible cable or wire.

4. A device according to claim 1, in which the elongate flexible member, band or strip is in the form of a mesh or grid created by weaving the elongate member, band or strip into a mat like structure.

5. A device according to, claim 1 in which the insulated electrically conductive wire is a copper, aluminium or titanium wire.

6. A device according to, claim 1 in which the insulated electrically conductive wire is coiled substantially around the length of the core.

7. A device according to claim 1, wherein the electrical impulses are picked up from the body of the wearer and from electrical fields in proximity to the body of the wearer.

* * * * *